US00PP35662P2

(12) United States Plant Patent
Van Dijk

(10) Patent No.: US PP35,662 P2
(45) Date of Patent: Feb. 20, 2024

(54) ***ANTHURIUM* PLANT NAMED 'AN2684808'**

(50) Latin Name: ***Anthurium andraeanum* L.**
Varietal Denomination: AN2684808

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,439

(22) Filed: Aug. 16, 2023

(51) Int. Cl.
*A01H 6/00* (2018.01)
*A01H 5/02* (2018.01)

(52) U.S. Cl.
USPC ..... Plt./365

(58) Field of Classification Search
USPC ..... Plt./365
CPC ..... A01H 6/00; A01H 5/02
See application file for complete search history.

*Primary Examiner* — Keith O. Robinson
(74) *Attorney, Agent, or Firm* — Jondle & Associates, P.C.

(57) ABSTRACT

A new *Anthurium* plant named 'AN2684808' particularly distinguished by having weakly blistered and strongly glossy, green with red venation and red tips, concave, cordate and durable spathes that retain the original color for a very long period of time, weakly glossy, dark green, elliptical cordate, durable leaves, dark red spadices with dark red tips, early and rich flowering continuously throughout the year, and a plant height of 70.0 cm to 80.0 cm is disclosed.

3 Drawing Sheets

Genus and species: *Anthurium andraeanum* L.
Variety denomination: 'AN2684808'.

BACKGROUND OF THE NEW PLANT

The present invention comprises a new and distinct variety of *Anthurium*, botanically known as *Anthurium andraeanum* L., and hereinafter referred to by the variety name 'AN2684808'. The new *Anthurium* plant is a product of a planned breeding program conducted by the inventor in Bleiswijk, the Netherlands. The objective of this breeding program was to create a new cut flower plant with a height of 70.0 cm to 80.0 cm having weakly blistered, strongly glossy, green with a red venation and red tips, concave and cordate, durable spathes.

The new variety originated from a cross-pollination made in November 2008 in Bleiswijk, the Netherlands. The female parent was a green *Anthurium* pot plant designated '05-011298-0003' (unpatented), and the male parent was a pink *Anthurium* pot plant designated '05-008812-0003' (unpatented).

A single plant was selected from the progeny of the stated cross in November 2011. Asexual reproduction of the new variety by tissue culture in 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 23, 2022 (Application no. 2022/2645), by Applicant who obtained the subject matter disclosed directly from the inventor. 'AN2684808' has not been made publicly available or sold anywhere in the world prior to the effective filing date of this application with the exception of sales or disclosures made one year or less before the effective filing date of this claimed invention by Applicant who obtained 'AN2684808' directly from the inventor.

SUMMARY OF THE INVENTION

The following are the most outstanding and distinguishing characteristics of this new variety when grown under normal horticultural practices in Bleiswijk, the Netherlands:

1) Weakly blistered, strongly glossy, green with a red venation and red tips, concave and cordate spathes;
2) Dark red spadices with dark red tips;
3) Weakly glossy, dark green, elliptical cordate leaves; and
4) Peduncle: anthocyanin coloration is strong.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 60-week-old plant grown in a greenhouse in Bleiswijk, the Netherlands, in May 2023. Colors in the photographs may differ from the color values cited in the detailed botanical description, which accurately describes the actual colors of the new variety.

DESCRIPTION OF THE NEW VARIETY

Figure 1:
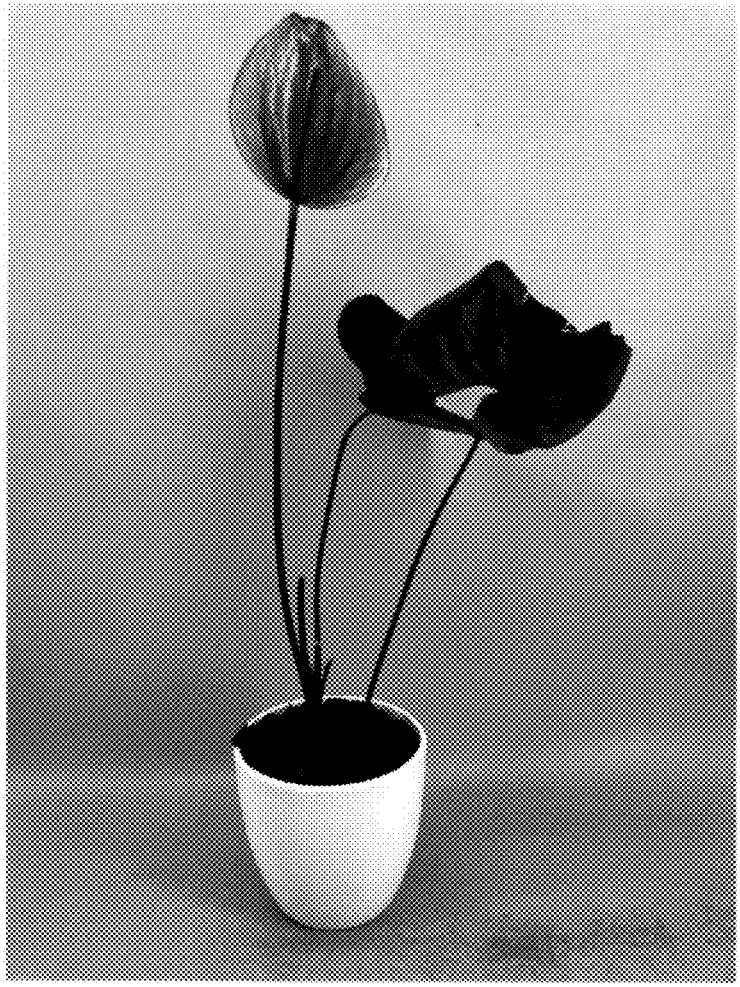
FIG. 1 shows the overall plant habit, including blooms, buds, and foliage.
Figure 2:
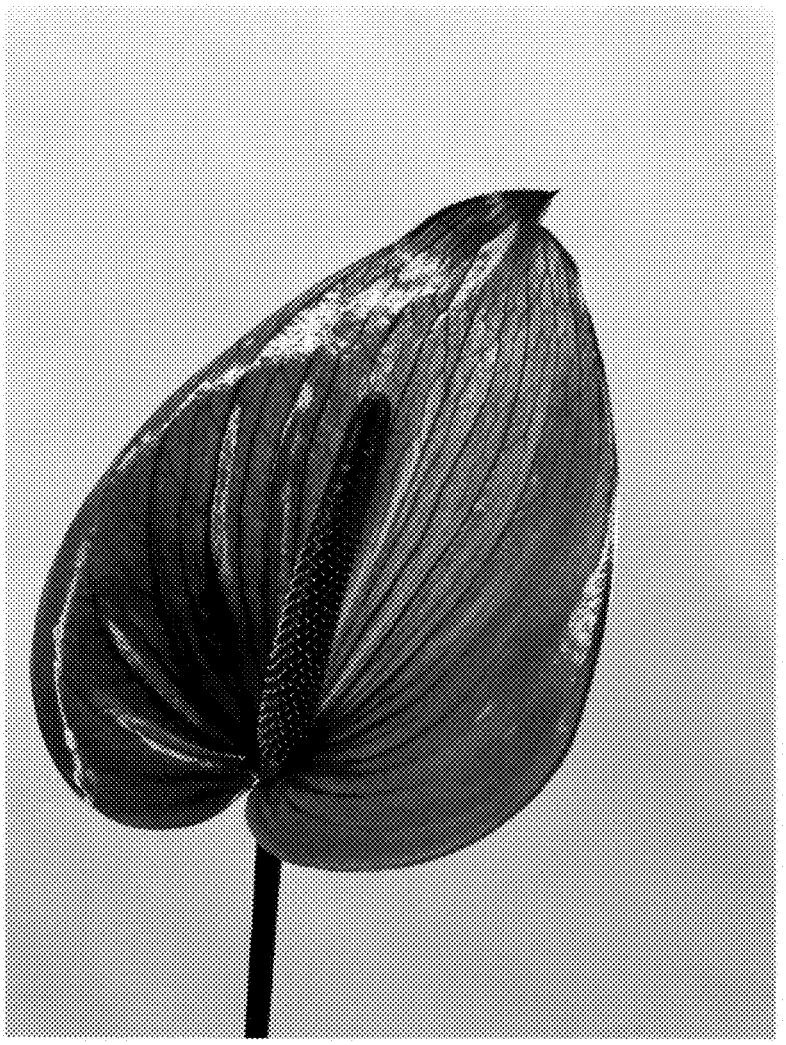
FIG. 2 shows a close-up of the mature spathe.
Figure 3:
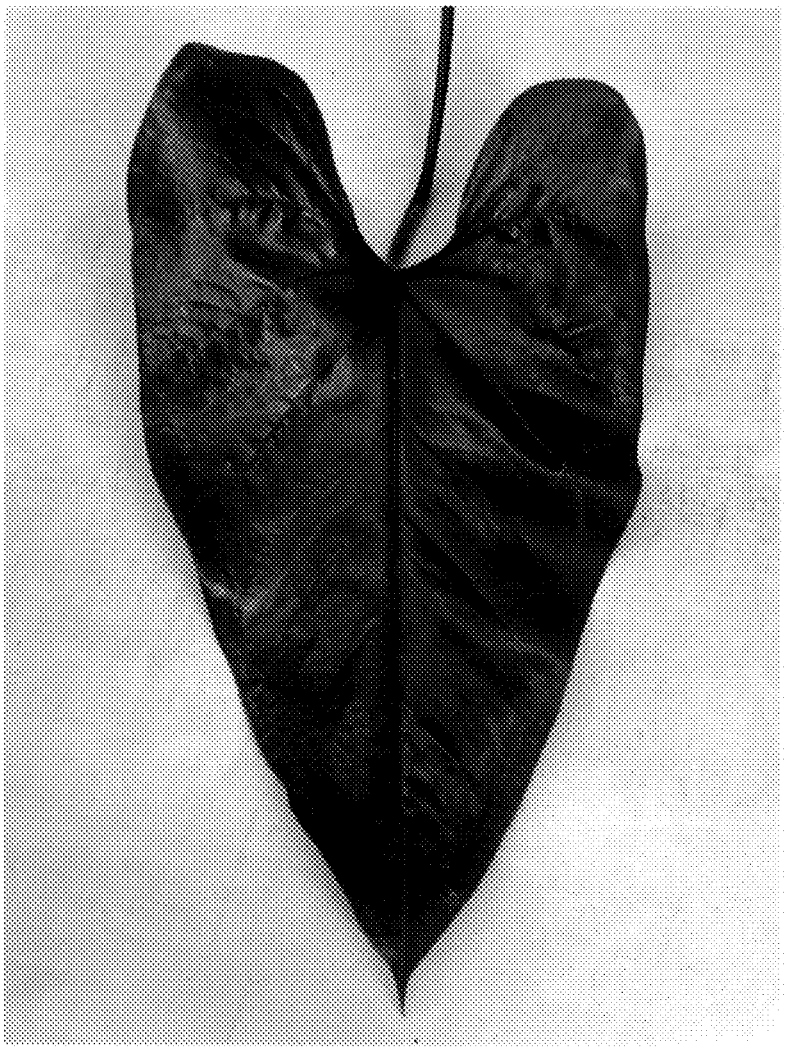
FIG. 3 shows a close-up of the upper leaf blade surface.

The following detailed description sets forth the distinctive characteristics of 'AN2684808'. The data which define these characteristics were collected from asexual reproductions carried out in Bleiswijk, the Netherlands. The plant history was taken on 60-week-old plants which were planted from tissue culture in 17-centimeter (diameter) pots and grown in a glass greenhouse between 19° C. and 24° C. Observations were made in May 2023. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2684808'.

Parentage:

*Female parent*.—*Anthurium* plant '05-011298-0003' (unpatented).

*Male parent*.—*Anthurium* plant '05-008812-0003' (unpatented).

Plant:

*Propagation*.—Tissue culture.

*Root description*.—Fleshy-creamy (RHS 161D) colored roots and small, hairy lateral roots having small yellow (RHS 7A) colored root tips.

*Time to produce a finished flowering plant*.—55 to 66 weeks after planting in a 17- cm (diameter) pot.

*Growth habit*.—Upright.

*Height* (*measured from soil, including inflorescence*).—70.0 cm to 80.0 cm.

*Width* (*measured from leaf tips*).—45.0 cm to 50.0 cm.

Leaves:

*Immature leaves*.—Length: 27.0 cm to 30.0 cm. Width: 18.0 cm to 20.0 cm. Color: Upper surface: Green (RHS 146B) with red tips (RHS 185A). Lower surface: Green (RHS 146C) with red tips (RHS 184B). Texture (both upper and lower surfaces): Leathery, soft, thin, and strongly glossy.

*Mature leaves*.—Length (fully expanded): 30.0 cm to 33.0 cm. Width: 20.0 cm to 22.0 cm. Shape: Elliptical cordate. Apex: Acuminate. Base: Cordate. Leaf blade angle with the petiole: Between 90 degrees and 110 degrees. Leaf margin: Entire. Color: Upper surface: Green (RHS 147A). Lower surface: Green (RHS 146B). Texture (on both surface): Leathery, thick, smooth, and weakly glossy. Venation: Pinnate veining; the mid-vein and primary veins (the veins which radiate out from junction of petiole and leaf) protrude at the underside of the leaf blade. Venation color: Upper surface: Dark red (RHS 187A). Lower surface: Green (RHS 187B).

*Lobes*.—Present. Arrangement: Leaf blade has two lobes extending past the petiole. The lobes are non-touching. Length of lobes of mature leaf blades: 8.0 cm to 9.0 cm. Width of lobes of mature leaf blades: 8.5 cm to 9.5 cm. Distance from petiole/leaf junction to highest point on lobes of mature leaf blades: 7.0 cm to 8.0 cm.

*Petiole*.—Cross-section: Round. Diameter: 0.5 cm to 0.6 cm. Length: 47.0 cm to 49.0 cm for a mature leaf size. Color: Mature leaf: Reddish-brown (RHS 200B). Immature leaf: Green (RHS 144A) with a red shade (RHS 181A) on the front side. Cataphyll color surrounding the petiole: Outside: Green (RHS 144C) at the base, red (RHS 178A) and dark red (RHS 183A) toward the tips. Inside: Light yellow-green (RHS 145D).

*Geniculum*.—Length: 4.0 cm to 5.0 cm. Width: 0.6 cm to 0.7 cm. Color: Green (RHS 144B) and dark red (RHS 187B) in the front.

Inflorescence:

*Arrangement*.—Single.

*Flowering habit* (*length of flowering season*).—Continuous.

*Number of inflorescences per plant*.—5 to 7 flowers in a period of one year.

*Fragrance*.—Absent.

*Longevity of inflorescence on plant*.—35 to 40 days.

Spathe:

*Buds*.—The spathe is tightly rolled around the spadix and extrudes from the peduncle sheath.

*Arrangement*.—Spathe angle with the peduncle is between 160 degrees and 170 degrees; the spathe stands on a wiry peduncle about 5.0 cm to 10.0 cm above the foliage.

*Shape*.—Cordate.

*Apex*.—Caudate.

*Base*.—Cordate.

*Texture*.—Weakly blistered and strongly glossy.

*Margin*.—Undulated.

*Size*.—Length: 13.0 cm to 14.0 cm. Width: 16.0 cm to 17.0 cm.

*Lobes*.—Present. Arrangement: The spathe has two lobes extending past the peduncle. The lobes are incurved, but not touching. Length: 1.5 cm to 2.5 cm. Width: 4.5 cm to 5.5 cm.

*Color*.—Just fully open: Upper surface: Green (RHS 144A) with red venation (RHS 183B) and red tips (RHS 46A). Lower surface: Green (RHS 144A) on one side and RHS 144B on the other side; diluting red (RHS 184B) at the tips and margins. This green color remains for a very long period, at least more than 30 weeks after opening.

Peduncle:

*Shape*.—Erect.

*Cross-section*.—Round.

*Length*.—56.0 cm to 61.0 cm.

*Diameter*.—0.6 cm to 0.7 cm.

*Color*.—Brown (RHS 200C).

Flowering time:

*General*.—One small, rooted, untreated tissue culture plant of 4.0 cm tall will flower for the first time, depending on the season, after 30 to 35 weeks.

Spadix:

*Size*.—Length: 8.0 cm to 9.0 cm (depending on flower size). Width (at apex): 0.7 cm to 0.9 cm. Width (at base): 1.0 cm to 1.2 cm.

*Shape*.—Columnar.

*Angle of spadix tip with peduncle*.—160 degrees to 180 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: Dark red (RHS 183B). Mature: Dark red (RHS 187B). Ages to: Brown (RHS 200C).

Flowers:

*Quantity per spadix*.—490 to 540.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 186C.

Reproductive organs:

*Stamens*.—Not visible.

*Pollen amount*.—Absent.

*Pistil*.—Quantity: 450 to 500. Length: Less than 0.01 cm. Color: RHS 186C.

*Style*.—Not observed to date.

*Stigma*.—Shape: Ovoid. Diameter: Less than 0.01 cm. Color: RHS 186C.

*Ovary*.—Rarely visible.

*Ovary color*.—Not measured.

Fruit and seed set: Fruit and seed production has not been observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2684808' differs from the female parent plant '05-011298-0003' (unpatented) in that 'AN2684808' has green, strongly glossy spathes and very long, dark red spadices, whereas '05-011298-0003' has pink, very weak glossy spathes and very long red-purple spadices.

'AN2684808' differs from the male parent plant '05-008812-0003' (unpatented) in that 'AN2684808' has large, cordate spathes and the basal part of the spadices are very long in length and dark red, whereas '05-008812-0003' has medium, orbicular cordate spathes and the basal part of the spadices are short to medium in length and red purple.

'AN2684808' differs from the similar commercial variety 'ANTHILZOR' (unpatented) in that 'AN2684808' has green spathes and strong glossy, dark red spadices, whereas 'ANTHILZOR' has pink spathes and very weak glossy, red purple spadices.

'AN2684808' differs from the similar commercial variety 'AN2886834' (unpatented) in that 'AN2684808' has green, cordate spathes and very strong anthocyanin coloration of the peduncle, whereas 'AN2886834' has light green, orbicular cordate spathes and very weak to weak anthocyanin coloration of the peduncle.

I claim:

1. A new and distinct variety of *Anthurium* plant named 'AN2684808', substantially as illustrated and described herein.

* * * * *